(12) United States Patent
Burlew et al.

(10) Patent No.: US 10,882,084 B2
(45) Date of Patent: Jan. 5, 2021

(54) SHIELDED CONTAINMENT CABINET AND METHOD OF USE

(71) Applicants: Joseph Burlew, Tiki Island, TX (US); Joe L. Savoy, Houston, TX (US)

(72) Inventors: Joseph Burlew, Tiki Island, TX (US); Joe L. Savoy, Houston, TX (US)

(73) Assignee: Joes Holdings LLC, Houston, TX (US)

( * ) Notice: Subject to any disclaimer, the term of this patent is extended or adjusted under 35 U.S.C. 154(b) by 0 days.

(21) Appl. No.: 16/192,010

(22) Filed: Nov. 15, 2018

(65) Prior Publication Data
US 2020/0156123 A1    May 21, 2020

(51) Int. Cl.
| B08B 15/02 | (2006.01) |
| A61B 90/70 | (2016.01) |
| B08B 3/02 | (2006.01) |
| B25J 21/02 | (2006.01) |

(52) U.S. Cl.
CPC ............ B08B 15/026 (2013.01); A61B 90/70 (2016.02); *A61L 2202/122* (2013.01); *A61L 2202/16* (2013.01); *B08B 3/026* (2013.01); *B08B 2203/0211* (2013.01); *B08B 2203/0264* (2013.01); *B25J 21/02* (2013.01)

(58) Field of Classification Search
CPC .................. B08B 15/026; B08B 3/026; B08B 2203/0264; B08B 2203/0211; B08B 3/106; B08B 3/02; B08B 3/14; A61B 90/70; A61L 2202/122; A61L 2202/16; A61L 2202/17; B25J 21/02; B09B 3/00
USPC ........................................................ 312/209
See application file for complete search history.

(56) References Cited

U.S. PATENT DOCUMENTS

| 3,542,592 | A | * | 11/1970 | Zweig ..................... B41B 11/00 134/1 |
| 3,679,483 | A | * | 7/1972 | Zweig ..................... B41B 11/00 134/46 |
| 3,874,754 | A |   | 4/1975 | Saunders |
| 4,026,286 | A | * | 5/1977 | Trexler ................ A61G 10/005 128/205.26 |
| 4,300,318 | A | * | 11/1981 | Brown ...................... B24C 3/02 451/38 |
| 4,676,261 | A | * | 6/1987 | Blaul .................... B08B 15/026 134/104.4 |
| 4,886,081 | A | * | 12/1989 | Blaul ...................... B08B 3/006 134/18 |
| 4,928,440 | A | * | 5/1990 | Hughes ..................... B24C 9/00 451/456 |
| 4,938,933 | A |   | 7/1990 | Perrot |
| 5,107,876 | A | * | 4/1992 | Ozyjiwsky ............ B08B 15/026 134/111 |
| 5,143,102 | A | * | 9/1992 | Blaul ...................... B08B 3/006 134/113 |

(Continued)

FOREIGN PATENT DOCUMENTS

WO   WO-2018046878 A1 * 3/2018 ............... A61L 2/10

OTHER PUBLICATIONS https://www.terrauniversal.com/glove-boxes/glove-ports.php.
(Continued)

*Primary Examiner* — Hiwot E Tefera
(74) *Attorney, Agent, or Firm* — Ira Domnitz

(57) ABSTRACT

A shielded containment cabinet device for use for the cleaning under high visibility and high protection for user, while using reduction flow pressurized water for cleaning of materials.

14 Claims, 4 Drawing Sheets

(56) References Cited

U.S. PATENT DOCUMENTS

| | | | |
|---|---|---|---|
| 5,320,199 A | 6/1994 | Griffiths | |
| 5,460,564 A * | 10/1995 | Bowes | B24C 9/00 312/263 |
| 5,858,305 A | 1/1999 | Malchesky | |
| 6,368,206 B1 | 4/2002 | Hunter | |
| 6,558,620 B1 | 5/2003 | Sanford | |
| 6,582,654 B1 | 6/2003 | Kral | |
| 6,585,943 B1 | 7/2003 | Sanford | |
| 6,610,251 B1 | 8/2003 | Kanno | |
| 6,814,932 B2 | 11/2004 | Hlebovy | |
| 8,282,895 B2 * | 10/2012 | Miller | G01N 35/1002 137/259 |
| 9,072,805 B1 | 7/2015 | Leight | |
| 9,138,115 B2 | 9/2015 | Stryker | |
| 9,433,695 B2 | 9/2016 | Aamodt | |
| 9,724,688 B2 * | 8/2017 | Kobayashi | B01L 1/04 |
| 2008/0210276 A1 * | 9/2008 | Porter | B08B 3/006 134/198 |
| 2008/0278041 A1 | 11/2008 | Lloyd | |
| 2011/0132404 A1 * | 6/2011 | Lutz | A61L 2/025 134/19 |
| 2013/0323140 A1 * | 12/2013 | Motadel | B01L 3/0275 422/524 |
| 2014/0165309 A1 | 6/2014 | Frey | |
| 2015/0239016 A1 * | 8/2015 | Spencer | B08B 3/106 134/34 |
| 2016/0039099 A1 * | 2/2016 | Kobayashi | C12M 37/00 422/565 |
| 2016/0074911 A1 * | 3/2016 | Dore | B29C 64/35 134/56 R |
| 2016/0106209 A1 * | 4/2016 | Miller | A61M 16/0003 312/209 |
| 2016/0157696 A1 * | 6/2016 | Safavi | B01L 3/0275 134/1 |
| 2016/0288125 A1 * | 10/2016 | Lang | B08B 15/026 |
| 2017/0100498 A1 * | 4/2017 | Sobhy | B01D 46/0038 |
| 2018/0147577 A1 * | 5/2018 | Shinya | G01N 15/1459 |
| 2018/0236672 A1 * | 8/2018 | Scotchmer | G21F 7/041 |
| 2018/0259261 A1 * | 9/2018 | Kim | A47K 1/00 |
| 2019/0184432 A1 * | 6/2019 | Dore | B01D 35/02 |

OTHER PUBLICATIONS https://www.google.com/search?q=medical+cabinet+with+glove.
https://www.google.com/search?q=medical+cabinet+with+glove+por.
https://www.google.com/search?tbm=isch&q=medical+cabinet+with.
https://www.coleparmer.com/i/electro-tech-systems.
www.novatech-usa.com.

* cited by examiner

SHIELDED CONTAINMENT CABINET AND METHOD OF USE

CROSS-REFERENCE TO RELATED APPLICATIONS

Not applicable

STATEMENT REGARDING FEDERALLY SPONSORED RESEARCH

Not applicable.

BACKGROUND

In several embodiments, the present invention solves the problems posed by standard hospital instrument decontamination units, namely, in conventional decontamination units there is a need to submerge surgical instruments under water and spray said instruments with a spray gun, while the instruments are under water. One disadvantage of this technique is that it is very difficult to see if instruments are clean when they are under water. Another disadvantage of this cleaning process is that water can be splashed onto a user when spraying with a water gun at instruments under water. Another disadvantage is that this process is time consuming and not portable.

The present invention, in several embodiments, enhances visual clarity as well as increases safety by preventing the cleaning process from splashing materials on the cleaning user. This is accomplished by utilizing a portable wash assembly with a viewing port, which allows for viewing of instruments while safely cleaning them in a contained area above water. The portability of the invention allows for use and hook up in a variety of locations.

The present invention is distinguished from the following prior art pieces in many ways.

U.S. Pat. No. 5,320,199 is developed for laparoscopic instrumentation only. The present invention allows for cleaning of all tools.

U.S. Pat. No. 5,858,305 is an automated sterilization device. The present invention is a manual pre-cleaning device for surgical instruments.

U.S. Pat. No. 6,368,206 is a device for lab experiments. The present invention is a manual pre-cleaning device for surgical instruments.

U.S. Pat. No. 3,874,754 is a sterile work environment for bio-research. The present invention is a manual pre-cleaning device for surgical instruments.

U.S. Pat. No. 4,938,933 is a device for use by surgeons and physicians for sterilization or disinfection of solid instrumentation with a pressurized diffusion of nebulized disinfection product. The present invention is a manual pre-cleaning device for surgical instruments.

U.S. Pat. No. 6,585,943 is a fluid delivery system for an automated processor. The present invention is a manual pre-cleaning device for surgical instruments.

U.S. Pat. No. 6,610,251 is a pressurized cleaning vessel. The present invention is a manual pre-cleaning device for surgical instruments.

U.S. Pat. No. 6,814,932 is a fluid delivery system for an automated processor. The present invention is a manual pre-cleaning device for surgical instruments.

U.S. Pat. No. 9,072,805 is a gas decontamination device with heating elements. The present invention is a manual pre cleaning device for surgical instruments.

U.S. Pat. No. 9,138,115 is a device for environmental cleaning and not the cleaning of surgical instruments. The present invention is a manual pre-cleaning device for surgical instruments.

U.S. Pat. No. 9,433,695 is a dry fog biocide agent with a vibrator that oscillates at ultrasonic frequencies. The present invention is a manual pre-cleaning device for surgical instruments containing no chemicals or vibration techniques.

US2008/0278041 is a biohazard containment cabinet for lab use with air filters and air flow control. The present invention is a manual pre-cleaning device for surgical instruments.

US2011/0132404 is a device for only cleaning laparoscopic instruments with heat fluids and sonic energy for interior cleaning and ultrasonic mechanical energy for exterior cleaning of the outside of the instrument. The present invention is a manual pre-cleaning device for surgical instruments with no chemicals and no vibrations.

US2014/0165309 is an apparatus that is electromechanically driven for cleaning device in surgical field for recovery of material. Our unit is a manual pre-cleaning device for surgical instruments; there are no electromechanically driven applications.

U.S. Pat. No. 6,582,654 is for a microbial decontamination of a device with at least one internal passage scope cleaner. The present invention is a manual pre-cleaning device for surgical instruments.

U.S. Pat. No. 6,558,620 is a microbial decontamination and rinsing of lumen device such as endoscopes. The present invention is a manual pre cleaning device for surgical instruments.

SUMMARY

The present invention is a new and novel design for a manual pre-cleaning device for surgical instruments. In several embodiments, the present invention is a high visibility, high pressure prewash and scrub that minimizes staff exposure to aerosolization. In several embodiments, the present invention utilizes a wash assembly with a viewing port to allow for safe cleaning of surgical instruments in a contained area above water. In some embodiments, the present invention can be scaled to house larger objects in its interior. In several embodiments, the present invention can be used to wash non-surgical items. In several embodiments, the present invention can be used to wash biological entities.

In one embodiment, the concept of the device is the gross cleaning under high visibility and high protection for user, while using reduction flow of pressurized water. In many medical applications, it is a pre-step to the IFU (Instructions for Use) to clean surgical instruments post-use. In several embodiments, the flushing and brushing of cannulated items, usually done under water and in a sink, can now be done in a lighted containment field, which protects user from possible splash of contaminated remains from surgical use. In some embodiments, the unit can be loaded from either side, using the sliding shelf for ergonomic assistance to user. There is a pressure nozzle that connects to the facility house water that has multiple tips for different size applications. Storage for brushes is available inside unit at the lower front.

In several embodiments, the present invention is a shielded containment cabinet device comprising: a wheel base assembly; said wheel base assembly further comprising; a storage cabinet; a storage cabinet door; a storage cabinet bottom panel; wheels; and a drain column; an upper wash assembly; said upper wash assembly further comprising; a wash cabinet with a window portal; a sliding tray with tray handles; a sleeve portal; a window with a window cover; a spray gun; a drain base; and a light in electrical communication with a light fixture; wherein, said upper wash assembly is located on, and in mechanical communication with, said wheel base assembly. In several embodiments, said sliding tray with tray handles is insertable and removable from said wash cabinets. In several embodiments, said drain base is in fluid communication with said drain column to allow for fluid flow in operation. In several embodiments, said spray gun is attached to said wash cabinet via a hook mount. In several embodiments, said light fixture is located on the top of said wash cabinet. In several embodiments, said sliding tray is on a track. In several embodiments of the present invention, the sleeves are replaced with hospital grade gloves. In several embodiments, the drain can be covered with a filter or screen during use to catch larger solid objects.

In several embodiments, the present invention is a method for use of a shielded containment cabinet device comprising the steps of: obtaining a shielded containment cabinet comprising; a wheel base assembly; said wheel base assembly further comprising; a storage cabinet; a storage cabinet door; a storage cabinet bottom panel; wheels; and a drain column; an upper wash assembly; said upper wash assembly further comprising; a wash cabinet with a window portal; a sliding tray with tray handles; a sleeve portal; a window with a window cover; a spray gun; a drain base; and a light in electrical communication with a light fixture; wherein, said upper wash assembly is located on, and in, mechanical communication with said wheel base assembly; loading materials for wash onto said sliding tray; placing said sliding tray into said wash cabinet; washing said materials on said tray by the process of having a user put their hand in at least one portal, and activating said spray gun to spray water on said materials. In some embodiments, the method further comprises removing said tray from said wash cabinet. In some embodiments, the method further comprises draining said spray water in said wash cabinet via opening said drain base and having said spray water flow through said drain base and into said drain column.

In several embodiments, the portability of the present invention allows for fluid hookups to various washing stations in various locations with decreased downtime for fluid hookup and device actuation.

BRIEF DESCRIPTION OF THE DRAWING

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
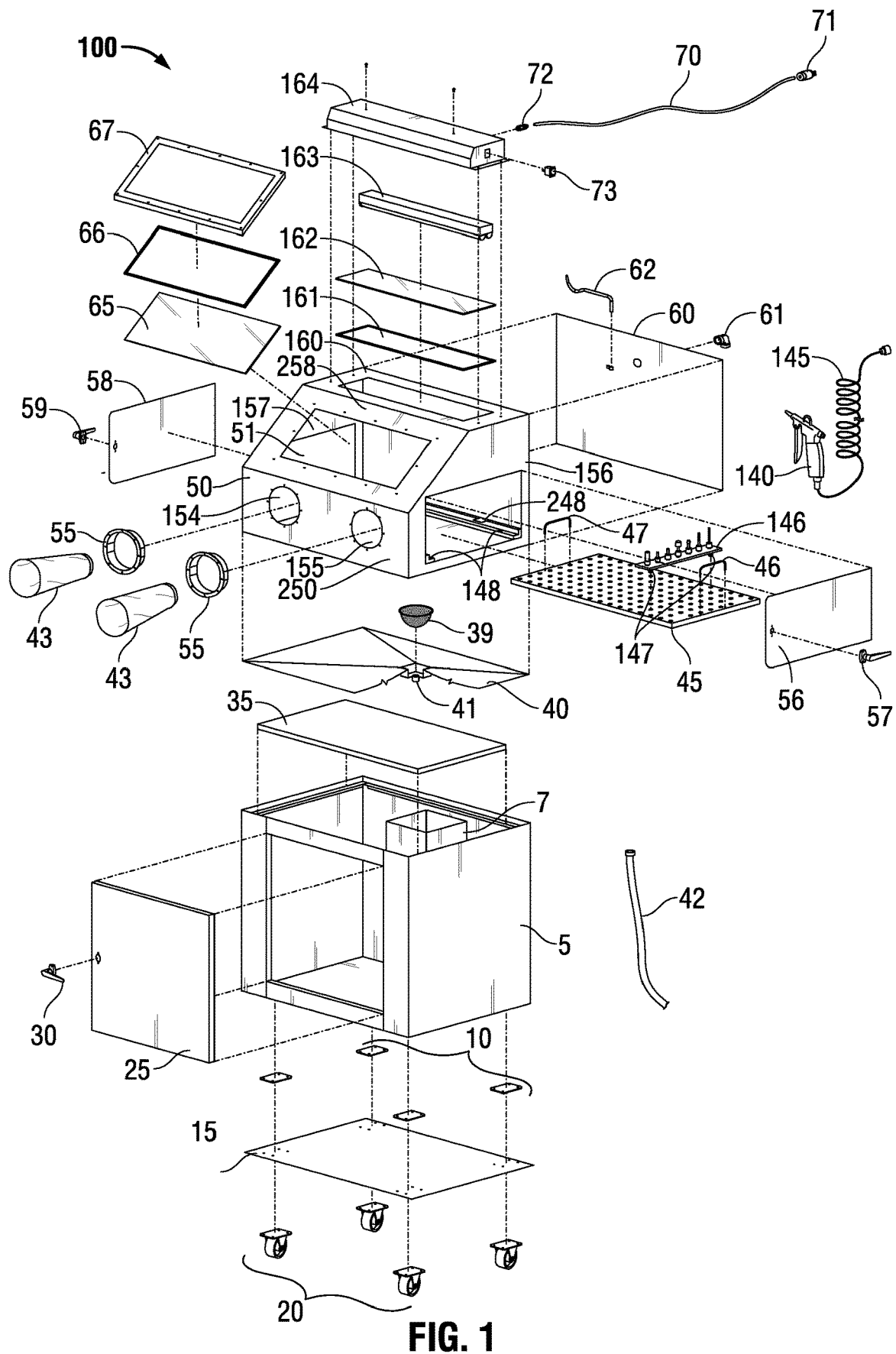
FIG. 1 is a view of one embodiment of the present invention in exploded view.

One or more illustrative embodiments, incorporating the invention disclosed herein, are presented below. Applicant has created a revolutionary and novel decontaminating washing cabinet and method of use of the same.

In the following description, certain details are set forth such as specific quantities, sizes, etc., so as to provide a thorough understanding of the present embodiments disclosed herein. However, it will be evident to those of ordinary skill in the art that the present disclosure may be practiced without such specific details. In many cases, details concerning such considerations, and the like, have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. Drawings are not necessarily to scale, and arrangements of specific units in the drawings can vary.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless, or essentially meaningless, the definition should be taken from Webster's Dictionary, 11th Edition, 2008. Definitions, and/or interpretations, should not be incorporated from other patent applications, patents, or publications, related or not, unless specifically stated in this specification or if the incorporation is necessary for maintaining validity. Specifically defined terms: As utilized herein, "glove(s)" or "sleeve(s)" are medical grade gloves or sleeves rated for use with medical glove boxes that could contain body materials, parts, or fluids.

Certain terms are used in the following description and claims to refer to particular system components. As one skilled in the art will appreciate, different persons may refer to a component by different names. This document does not intend to distinguish between components that differ in name, but not function. The drawing figures are not necessarily to scale. Certain features of the invention may be shown exaggerated in scale, or in somewhat schematic form, and some details of conventional elements may not be shown, all in the interest of clarity and conciseness.

Although several preferred embodiments of the present invention have been described in detail herein, the invention is not limited hereto. It will be appreciated by those having ordinary skill in the art that various modifications can be made without materially departing from the novel and advantageous teachings of the invention. Accordingly, the embodiments disclosed herein are by way of example. It is to be understood that the scope of the invention is not to be limited thereby.

Figure 2:
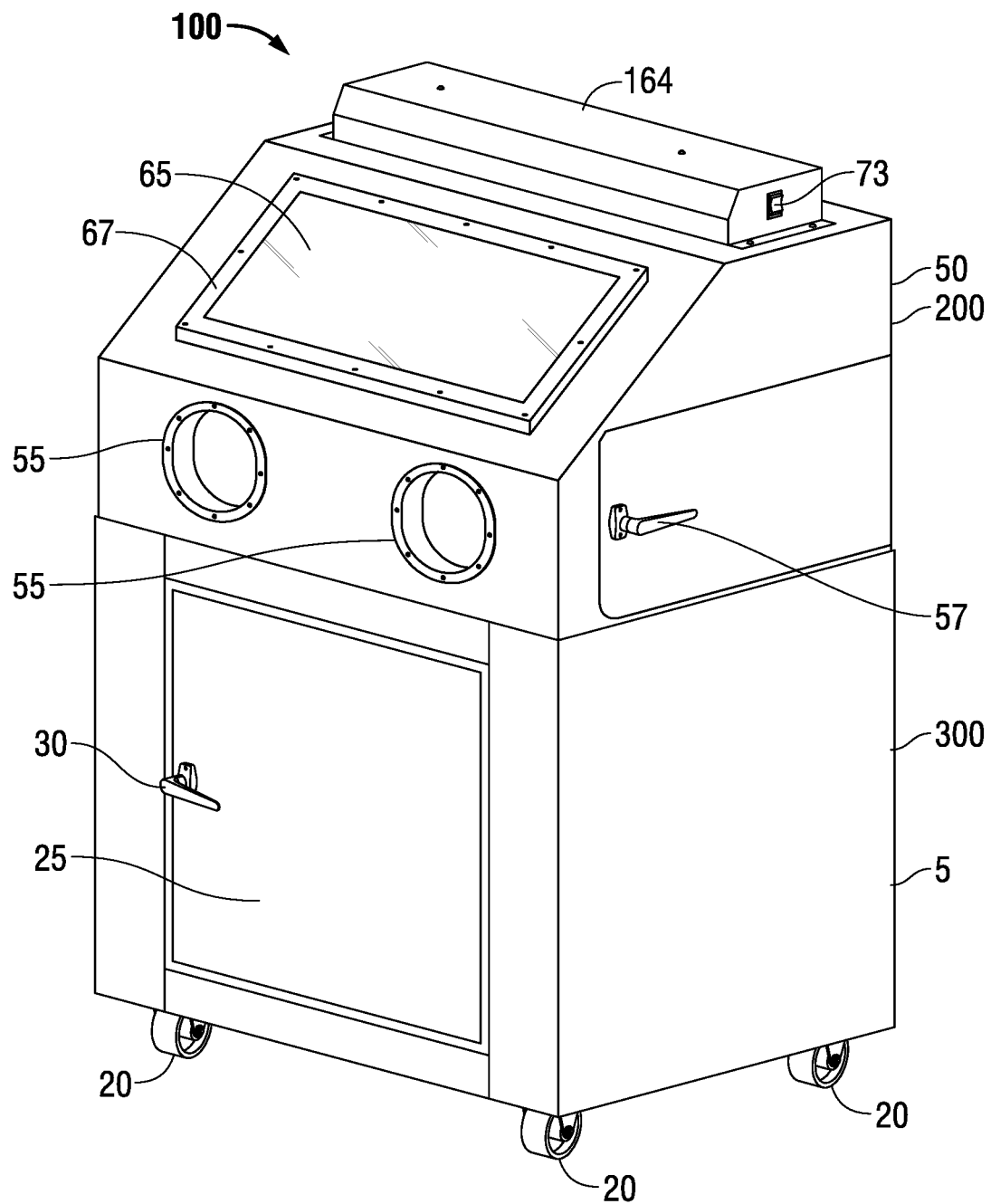
FIG. 2 is an assembled view of one embodiment of the present invention in partial side perspective.

FIG. 1 is an exploded view of one embodiment of the present invention. As illustrated, a shielded containment cabinet device, or assembly 100 is comprised of a wheeled base assembly 300 and upper wash assembly 200 (FIG. 2). As shown, bottom base or storage cabinet bottom panel 15 is preferably flat and moisture resistant. In many embodiments, wheels 20 are attached to the substantially lower portion of bottom base or storage cabinet bottom panel 15. In many embodiments, wheels 20 are rubber medical wheels. In many embodiments, wheels 20 can lock in place to prevent a shielded containment cabinet device, or assembly 100 movement. In many embodiments, bottom base or storage cabinet bottom panel 15 is comprised of a metal or plastic material known in the art for use in medical applications. In many embodiments, wheels 20 can attach to bottom base or storage cabinet bottom panel 15 as known in the art for cabinet movement.

Further shown in FIG. 1 are wheel support plates 10. Wheel support plates 10 are preferably designed to be placed above bottom base or storage cabinet bottom panel 15 and used to adhere bottom base or storage cabinet bottom panel 15 to lower storage cabinet 5. As shown, in several embodiments, lower storage cabinet 5 is preferably constructed with a rectangular box shape with the upper surface open, and the front facing surface with an orifice designed to contain a storage cabinet door 25 with handle 30. In many embodiments of the present invention, the shape of lower storage cabinet 5 can vary. In many embodiments, lower storage cabinet 5 is designed with a fluid egress column 7, with three sides and a back opening for maneuvering and attaching and drainage hose 42. In many embodiments, cabinet 5 is made of lightweight metal or plastic capable of supporting wash assembly 200 (FIG. 2). In several embodiments, storage cabinet door 25 is attached to lower storage cabinet 5 in a manner known in the art such that storage cabinet door 25 can open and materials be stored in said lower storage cabinet 5 in a manner known in the art.

In several embodiments, lower storage cabinet 5 has a storage cabinet shelf 35. In some embodiments of the present invention, storage cabinet shelf 35 forms a secondary shelf for lower storage cabinet 5. In several embodiments, storage cabinet shelf 35 is constructed of non-rusting metal alloy, stainless steel, or other non-oxidizing metal. In some embodiments, located above storage cabinet shelf 35 is drain foil or wash cabinet drain panel 40. In several embodiments, drain foil or wash cabinet drain panel 40 functions with drain 41 to allow drainage of liquids and materials from any decontamination run off. In several embodiments, drain foil or wash cabinet drain panel 40 is constructed of nonrusting metal alloy, stainless steel, or other non-oxidizing material. In many embodiments, drain foil or wash cabinet drain panel 40 is removable, replaceable, and separately cleanable from wash cabinet 50. In several embodiments, drain foil or wash cabinet drain panel 40 can attach to a drain tube 42 to allow for water to exit said decontamination assembly 100. Drain tube 42 is preferably of a type utilized in medical waste draining technology. In several embodiments, drain 41 can be covered with removable screen or filter 39. In several embodiments, screen or filter 39 is a standard filter or screen for use in preventing solids, such as screws, metal objects or other particles from flowing into drain tube 42 and potentially getting lost.

In several embodiments, there is a decontaminating housing or wash cabinet 50. In several embodiments, decontaminating housing or wash cabinet 50 is comprised of non-rusting metal alloy, stainless steel, or other non-oxidizing metal. In several embodiments, decontaminating housing or wash cabinet 50 has two side door ports 156 and 157, respectively. Side door ports 156 and 157 are preferably constructed to allow for materials to pass into said side door ports, such as, but not limited to, perforated drain tray 45. In many embodiments, the perforated drain tray 45 is constructed of non-rusting metal alloy, stainless steel, or other non-oxidizing metal. In many embodiments, perforated drain tray 45 is designed with rack holders or tray handles 46 and 47. In many embodiments of the present invention, the interior of wash cabinet 50 has two opposing guide rails or track 148, which can slideably guide perforated drain tray 45 to allow for said tray 45 to move through the ports 156 and/or 157 without slipping or falling out of the wash cabinet 50. In many embodiments, there are guide stops 248 which are designed to allow only limited movement of tray 45 in and out of wash cabinet 50. In some embodiments, stops 248 can be loosened or removed to allow for full removal of tray 45. In some embodiments, said sliding tray with tray handles is in slideable communication with said guide track 148.

In many embodiments, rack holders or tray handles 46 and 47 are constructed of non-rusting metal alloy, stainless steel, or other non-oxidizing metal. In several embodiments, rack holders or tray handles 46 and 47 are constructed as substantially inverted "U" shapes with attachment to perforated base or sliding tray 45. In several embodiments, perforated base or sliding tray 45 is constructed of hospital grade materials for use with drainage of biological organisms and fluids. In several embodiments of the present invention, perforated drain tray 45 can be inserted into side door ports 156 or 157. In several embodiments of the present invention, a nozzle rack 146 is modified with attachment stoppers 147 below the nozzle rack 146 to allow for said nozzle rack 146 to mechanically attach to sliding tray 45 in a manner that the nozzle rack 146 is in the wash cabinet 50 when the cabinet is in use.

In several embodiments of the present invention, door ports 156 and 157 are in mechanical communication with side doors 56 and 58, respectively to allow side doors 56 or 58 to be opened as needed when the a shielded containment cabinet device, or assembly 100 is in use. In some embodiments, side doors 56 and 58 have door handles 57 and 59. In some embodiments, side doors 56 and 58 are constructed of non-rusting metal alloy, stainless steel, or other non-oxidizing metal.

In some embodiments of the present invention, decontamination housing or wash cabinet 50 is constructed with front 257 and front slant 258. In many embodiments, front slant 258 is constructed with view port 51. In several embodiments, front 257 is constructed with sleeve ports 154 and 155. In many embodiments, sleeve ports 154 and 155 are designed to function as standard sleeve ports for a medical and waste disposal device, or sleeve/glove box, as known in the industry. Further illustrated are sleeve port cuffs 55. In several embodiments, sleeve port cuffs 55 function as standard sleeve port cuffs for a medical and waste disposal device, or sleeve/glove box, as known in the industry.

In several embodiments, sleeves 43 are attached to the sleeve port cuffs 55 inside of wash cabinet 50 in a manner to allow for sleeves 43 to be removed and cleaned, but also to insure that the sleeves 43 do not become detached during use of the cabinet for decontamination by a user. In some embodiments, sleeves 43 are full length medical gloves. In some embodiments, sleeves 43 are rubber sleeves that bunch at the wrist of a user when in use in a standard medical capacity.

As shown in FIG. 1, in some embodiments of the present invention, front slant 258 is constructed with a view port 51, which provides visibility to the interior of decontamination housing or wash cabinet 50. In several embodiments of the present invention, view port 51 is sealed and covered with an interior layer or glass window 65, followed by intermediate layer or foam gasket 66, and lastly followed by exterior transparent viewing panel or window cover 67.

Further illustrated in FIG. 1 is orifice 160 for light glass 161. In many embodiments, light glass 161 is of the type typically used in medical applications for lighting medical devices. In several embodiments, transparent plate 162 is inserted between light glass 161 and LED fixture 163. In several embodiments, LED light fixture 163 is of the type typically used in medical device technology. In several embodiments, located above LED light fixture 163, and in electronic communication with said light fixture, is housing light cover 164. In many embodiments, housing light cover 164 is designed in the manner typical for housing lighting for a medical device.

In several embodiments of the present invention, attached to LED light fixture 163 is electrical wire connector 72. Connected to wire connector 72, in standard fashion, is electrical wire 70. Attached to electrical wire 70 is standard electrical plug 71. In some embodiments, in electrical communication with housing light cover 164 is electrical switch 73.

In several embodiments, wash cabinet back panel 60 is comprised of materials typically utilized with medical cabinets and medical applications. In several embodiments, back panel 60 has a spray gun hook 62 as well as a 90° water connection elbow 61. In several embodiments, attached to cabinet back panel 60, is spray gun 140 with spray gun hose 145. Spray gun 140 is preferably designed to be of industry standard for a spray gun used for decontamination of medical appliances. In several embodiments, water connection elbow 61 connects with spray gun hose 145 as is known in the art.

FIG. 2 is an assembled view of one embodiment of the present invention in partial side perspective. In many embodiments, wheels 20 are attached to the substantially lower portion of bottom base or storage cabinet bottom panel 15 (FIG. 1). In many embodiments, wheels 20 are rubber medical wheels. As shown, in several embodiments, lower storage cabinet 5 is preferably constructed with a rectangular box shape with the upper surface open and the front facing surface with an orifice designed to contain a storage cabinet door 25 with handle 30. In many embodiments, cabinet 5 is designed with a fluid egress column 7 (FIG. 1). In many embodiments, fluid egress column 7 is a three sided column with an opening in the back of cabinet 5 so that drain hose 42 can be attached to drain 41 (FIG. 1) in a manner known in the art for draining of medical waste. In many embodiments, cabinet 5 is made of lightweight metal or plastic capable of supporting wash assembly 200. In several embodiments, storage cabinet door 25 is attached to lower storage cabinet 5 in a manner known in the art such that storage cabinet door 25 can open and materials be stored in said lower storage cabinet 5 in a manner known in the art.

Further illustrated are sleeve port cuffs 55. In several embodiments, sleeve port cuffs 55 function as standard sleeve port cuffs for a medical and waste disposal device, or sleeve/glove box, as known in the industry. In several embodiments of the present invention, view port 51 is sealed and covered with interior layer or glass window 65, followed by intermediate layer or foam gasket 66 (FIG. 1), and lastly followed by exterior transparent viewing panel or window cover 67. In several embodiments, located above LED light fixture 163 (FIG. 1), and in electronic communication with said light fixture, is housing light cover 164. In many embodiments, housing light cover 164 is designed in the manner typical for housing lighting for a medical device. In several embodiments, decontaminating housing or wash cabinet 50 is comprised of non-rusting metal alloy, stainless steel, or other non-oxidizing metal.

As illustrated, a shielded containment cabinet device, or assembly 100 is comprised of a wheeled base assembly 300 and upper wash assembly 200. Further illustrated are sleeve port cuffs 55. In several embodiments, sleeve port cuffs 55 function as standard sleeve port cuffs for a medical and waste disposal device, or sleeve/glove box, as known in the industry. As shown, in several embodiments, lower storage cabinet 5 is preferably constructed with a rectangular box shape with the upper surface open and the front-facing surface with an orifice designed to contain a storage cabinet door 25 with handle 30.

Figure 3:
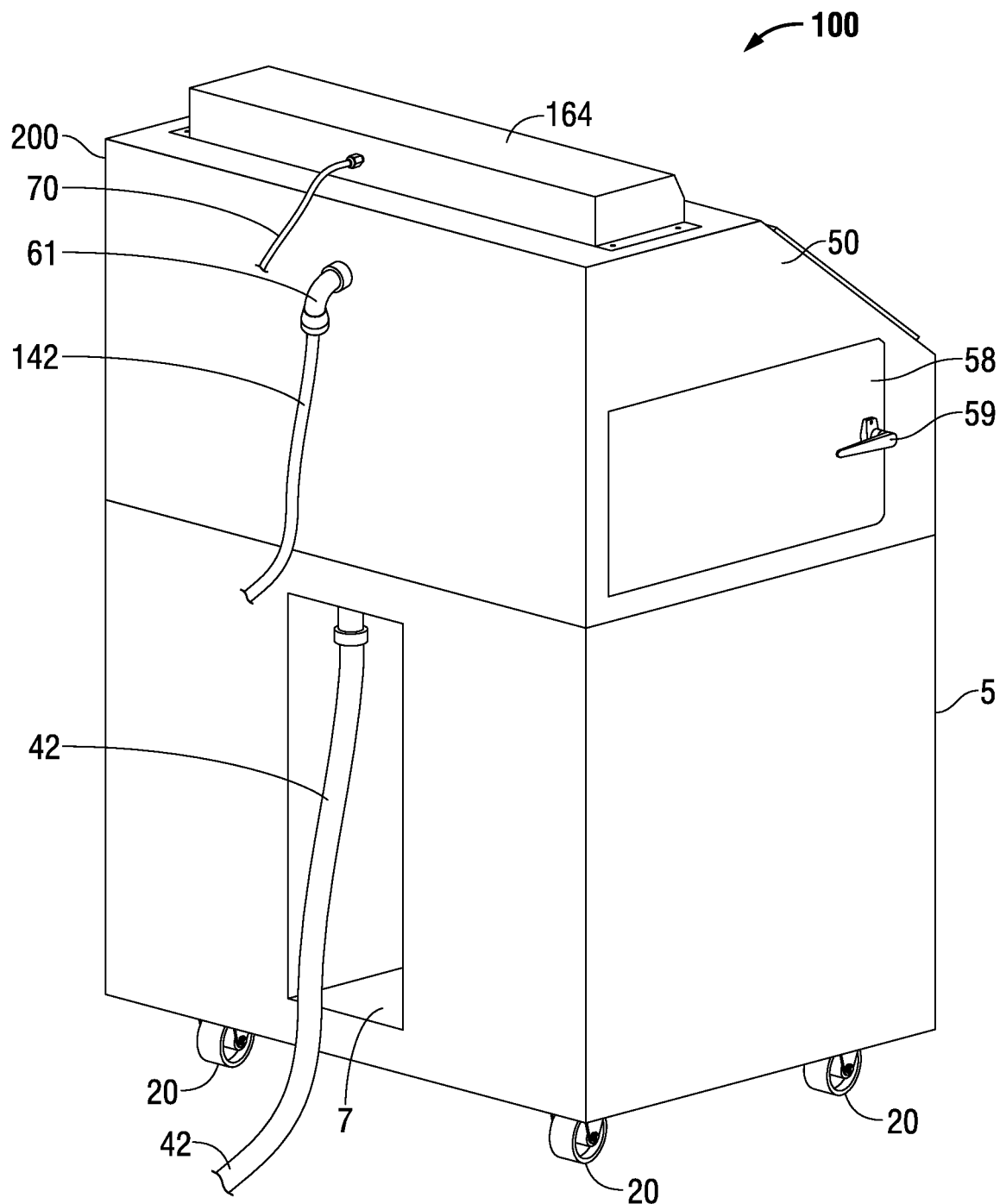
FIG. 3 is an assembled cross section view of one embodiment of the present invention in partial side perspective of the reverse side of the invention.

FIG. 3 is an assembled view of one embodiment of the present invention in partial side perspective rotated substantially 180 degrees from FIG. 2. In many embodiments, wheels 20 are attached to the substantially lower portion of bottom base or storage cabinet bottom panel 15 (FIG. 1). In many embodiments, wheels 20 are rubber medical wheels. As shown, in several embodiments, lower storage cabinet 5 is preferably constructed with a rectangular box shape with the upper surface open and the front-facing surface with an orifice designed to contain a storage cabinet door 25 with handle 30. In many embodiments, cabinet 5 is designed with a fluid egress column 7. In many embodiments, fluid egress column 7 is a three sided column with an opening in the back of cabinet 5 so that drain hose 42 can be attached to drain 41 (FIG. 1) in a manner known in the art for draining of medical waste. In many embodiments, cabinet 5 is made of lightweight metal or plastic capable of supporting wash assembly 200.

In several embodiments, located above LED light fixture 163 (FIG. 1) and in electronic communication with said light fixture is housing light cover 164. In many embodiments, housing light cover 164 is designed in the manner typical for housing lighting for a medical device. In several embodiments, there is a decontaminating housing or wash cabinet 50. In several embodiments, decontaminating housing or wash cabinet 50 is comprised of non-rusting metal alloy, stainless steel, or other non-oxidizing metal.

As illustrated, in some embodiments, decontamination spray hose 142 is attached to connection elbow 61 in a manner known in the art for fluid flow connection with a spray hose. Further illustrated is drainage hose 42 which is preferably designed to allow for water to exit said decontamination assembly 100. Drain tube 42 is preferably of a type utilized in medical waste draining technology. In some embodiments, drain tube 42 is comprised of hospital grade rubber.

Figure 4:
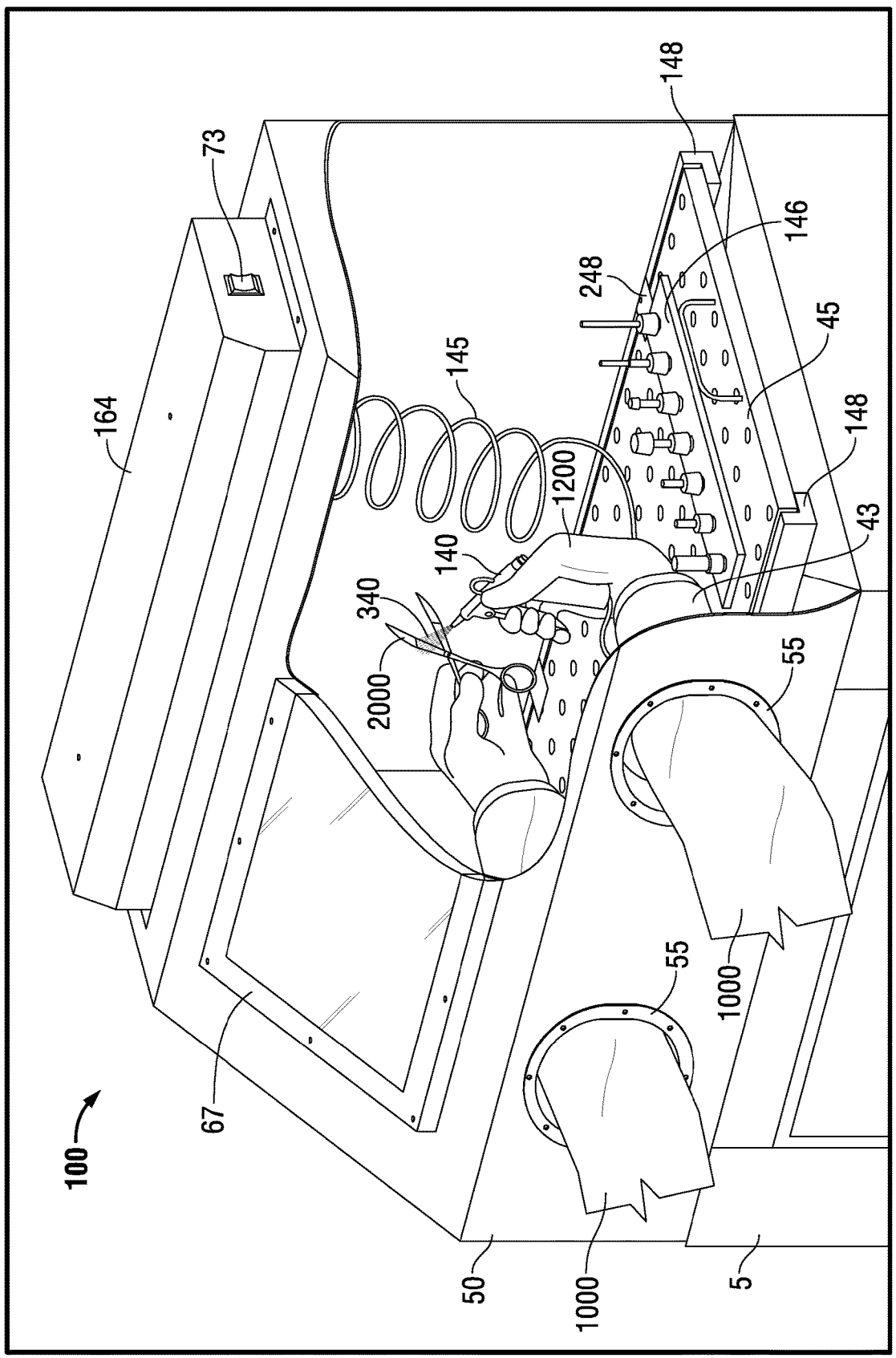
FIG. 4 is a partial cross-sectional assembled view of one embodiment of the present invention while in operation.

FIG. 4 illustrates one embodiment of the present invention in partial cross-section showing a user washing a surgical instrument. In one embodiment of the present invention, user can put their arms 1000 through port cuffs 55 on decontaminating housing or wash cabinet 50. In many embodiments, it is preferred that user will have medical gloves 1200 on their hands before inserting their arms 1000 through the port cuffs 55. In several embodiments, when the arms 1000 are pushed through port cuffs 55 they will engage sleeves 43. In several embodiments, sleeves 43 are of a design to constrict around the arms 1000 of a user in such a manner as to prevent any materials in cabinet 50 from touching or getting on the arms 1000 of a user when the a shielded containment cabinet device, or assembly 100 is in use. In several embodiments, sleeves 43 are made of hospital grade rubber.

As further illustrated in FIG. 4, a user is shown holding and washing a surgical instrument 2000. As illustrated, spray gun 140 sprays water 340 to clean and decontaminate the surgical instrument 2000. As shown in this embodiment, and as is advantageous over prior art, the user does not have to submerge surgical instrument 2000 in water 340 in order to decontaminate it. As further shown, in several embodiments, spray gun 140 is hooked up to spray hose 145.

As illustrated in FIG. 4, wash cabinet 50 has side doors 56 and 58 (FIG. 1) closed so that there is no spray from spray gun 140 that will spray outside of cabinet 50 when in use. Further shown, in FIG. 4, is nozzle rack 146 which is housed in wash cabinet 50 when in operation. Nozzle rack 146 offers a plurality of nozzle tips for use on the spray gun 140 for cleansing of surgical tools 2000 during operation. In several embodiments, guide stops 248 mechanically engage the holes in tray 45 to ensure that the nozzle rack 146 does not slip.

In several embodiments, FIG. 4 further illustrates track 148 which slideably engages tray 45. In many embodiments, there are guide stops 248 which are designed to allow only limited movement of tray 45 in and out of wash cabinet 50. In some embodiments, guide stops 248 can be loosened or removed to allow for full removal of tray 45. In several embodiments, LED light fixture 163 (FIG. 1) is of the type typically used in medical device technology. In several embodiments, located above LED light fixture 163, and in electronic communication with said light fixture, is housing light cover 164. In many embodiments, housing light cover 164 is designed in the manner typical for housing lighting for a medical device.

In several embodiments, the present invention is a shielded containment cabinet device, or assembly 100 with a wheel base assembly 300; a storage cabinet 5; a storage cabinet door 25; a storage cabinet bottom panel 15; wheels 20; and a drain column 7. In several embodiments the shielded containment cabinet device, or assembly 100 also has an upper wash assembly 200 with a wash cabinet 50 with a window portal 51 and a guide track 148; a sliding tray 45 with tray handles 46 and perforations; a sleeve portal 55; sleeves 43; a window 65 with a window cover 67; a spray gun 140; a drain base 40; and a light 163 in electrical communication with a light fixture 164. (See FIG. 1)

In several embodiments, the present invention operates[1] as follows: the shielded containment cabinet device, or assembly y 100 is moved to a location where use is desired. Drain hose 42 is attached to a standard drain (not shown) and to drain 41 in a manner as known in the art. Connection elbow 61 is attached to a decontamination spray hose 145 in a manner known in the art. It should be noted that connections to drain hose 42 and to spray hose 145 need not be in sequential order. In many embodiments, spray hose 145 is already attached to elbow 61 as known in the art, or it can be attached at this time. (See FIG. 1)

[1] It is assumed that proper medical protocol concerning the use of gloves and controlled materials will be observed during operations of the invention in most embodiments.

In several embodiments, a user will then open the doors 56 or 58 and slide the tray 45 about guide rails or track 148 and move tray 45 out of doors 56 or 58. A user can then either obtain surgical instruments 2000 for cleaning or set up the nozzle rack 146 on the tray 45 by attaching nozzle rack 146 to the holes on tray 45 via stoppers 248. Although, in some embodiments, it is not necessary to attach the nozzle rack 146 to tray 45. Once the tray 45 has been configured to a user's preference, the surgical instruments 2000 to be cleaned can be placed on tray 45, tray 45 slid back into cabinet 50 and doors 56 or 58 closed.

In several embodiments, the user can then slip their arms 1000 through sleeve port cuffs 55 and into sleeves 43. The user (assumed wearing gloves 1200 as required by protocol) can then use the spray gun 140 to spray water 340 on surgical instruments 2000 for cleaning and decontamination without having to submerge the surgical instrument 2000 under water. The user can safely view all functions in the cabinet 50 through viewing panel 67.

Water and waste materials from cleaning surgical instruments 2000, in several embodiments, will drain through the perforations in tray 45, through drain 41 (FIG. 1), and out of drain hose 42 (FIG. 3) in a manner as known in the art. When a user is done decontaminating surgical instruments 2000, the user can then open doors 56 or 58, slide out tray 45 and then remove surgical instruments 2000.

In several embodiments of the present invention, the methods and steps as outlined above have additional steps. In several embodiments, there is a step of loading materials, which may include non-surgical instruments, or other materials that can fit in cabinet 5, for washing onto said sliding tray 45. In several embodiments, there is the step of washing said materials on said tray 45 by the process of having a user put their arm in at least one sleeve 43, and activating said spray gun 140 to spray water 340 on said materials. In some embodiments, there is the step of being able to fully remove said sliding tray 45 from said wash cabinet 50. In several embodiments, there is the step of draining said spray water 340 in said wash cabinet 50 via opening said drain 41 and having said spray water 340 drain through said drain panel 40 and into said drain column 7. In several embodiments, the step of attaching a nozzle rack 146 with attachment stoppers 248 where said stoppers are in mechanical attachment with said perforations onto said sliding tray 45 prior to moving said sliding tray 45 into said wash cabinet 50.

While preferred embodiments have been shown, and described, modifications thereof can be made by one skilled in the art without departing from the scope or teaching herein. The embodiments described herein are exemplary only and are not limiting. Many variations and modifications of the system and apparatus are possible and will become apparent to those skilled in the art once the above disclosure is fully appreciated. For example, the relative dimensions of various parts, the materials from which the various parts are made, and other parameters can be varied. Accordingly, it is intended that the following claims be interpreted to embrace all such variations and modification.

The invention claimed is:
1. A shielded containment cabinet device comprising:
   a wheel base assembly;
      said wheel base assembly further comprising;
         a storage cabinet;
         a storage cabinet door;
         a storage cabinet bottom panel;
         wheels; and
         a drain column with three sides and a back opening;
   an upper wash assembly;
      said upper wash assembly further comprising;
         a wash cabinet with a window portal and a guide track;
         a sliding tray with tray handles and perforations;
         a sleeve portal;
         sleeves;
         a window with a window cover;
         a spray gun;
         two side door ports attached to two side doors;
         a drain base with a drain; and
         a light in electrical communication with a light fixture; wherein,
   said upper wash assembly is located on, and in mechanical communication with said wheel base assembly; wherein said sliding tray with tray handles can slide out either of said two side door ports attached to said two side doors via said guide track.

2. The shielded containment cabinet device of claim 1 further comprising:
guide stops; wherein
said sliding tray with tray handles is in slideable communication with said guide track and have limited motion as restricted by said guide stops.

3. The shielded containment cabinet device of claim 1 further comprising:
said drain base is in fluid communication with said drain column to allow for fluid flow in operation.

4. The shielded containment cabinet device of claim 1 further comprising:
said spray gun is attached to wash cabinet via a hook mount.

5. The shielded containment cabinet device of claim 1 further comprising:
said light fixture is located on the top of said wash cabinet.

6. The shielded containment cabinet device of claim 1 further comprising:
a nozzle rack with attachment stoppers where said stoppers are in mechanical attachment with said perforations on said sliding tray.

7. The shielded containment cabinet device of claim 1 further comprising:
said sleeves are comprised of medical grade gloves.

8. The shielded containment cabinet device of claim 1 further comprising:
a screen that can cover said drain wherein said screen prevents solids from flowing into said drain.

9. A method for use of a shielded containment cabinet device comprising the steps of:
obtaining a shielded containment cabinet comprising;
a wheel base assembly;
said wheel base assembly further comprising;
a storage cabinet;
a storage cabinet door;
a storage cabinet bottom panel;
wheels; and
a drain column with three sides and a back opening;
an upper wash assembly;
said upper wash assembly further comprising;
a wash cabinet with a window portal and a guide track;
a sliding tray with tray handles and perforations;
a sleeve portal;
sleeves;
a window with a window cover;
a spray gun;
two side door ports attached to two side doors;
a drain base with a drain; and
a light in electrical communication with a light fixture; wherein,
said upper wash assembly is located on, and in mechanical communication with said wheel base assembly;
loading materials for wash onto said sliding tray;
moving said sliding tray into said wash cabinet;
washing said materials on said tray by the process of having a user put their hand in at least one sleeve, and activating said spray gun to spray water on said materials; wherein
said sliding tray with tray handles can slide out either of said two side door ports attached to said two side doors via said guide track.

10. The method of claim 9 further comprising:
removing said sliding tray from said wash cabinet.

11. The method of claim 9 further comprising:
draining said spray water in said wash cabinet via opening said drain base and having said spray water drain through said drain base and into said drain column.

12. The method of claim 9 further comprising:
attaching a nozzle rack with attachment stoppers where said stoppers are in mechanical attachment with said perforations onto said sliding tray prior to moving said sliding tray into said wash cabinet.

13. The method of claim 9 further comprising:
covering said drain with a screen wherein said screen prevents solids from flowing into said drain.

14. The method of claim 9 further comprising:
inserting guide stops on said sliding tray with tray handles; wherein
said sliding tray with tray handles is in slideable communication with said guide track and have limited motion as restricted by said guide stops.

\* \* \* \* \*